US009079219B2

(12) United States Patent
Chen

(10) Patent No.: US 9,079,219 B2
(45) Date of Patent: Jul. 14, 2015

(54) THERAPEUTIC ULTRASOUND TRANSDUCER CHIP WITH INTEGRATED ULTRASOUND IMAGER AND METHODS OF MAKING AND USING THE SAME

(75) Inventor: Jingkuang Chen, Rochester, NY (US)

(73) Assignee: STC.UNM, Albuquerque, NM (US)

( * ) Notice: Subject to any disclaimer, the term of this patent is extended or adjusted under 35 U.S.C. 154(b) by 866 days.

(21) Appl. No.: 12/920,271

(22) PCT Filed: Feb. 27, 2009

(86) PCT No.: PCT/US2009/035601
§ 371 (c)(1), (2), (4) Date: Nov. 24, 2010

(87) PCT Pub. No.: WO2009/111351
PCT Pub. Date: Sep. 11, 2009

(65) Prior Publication Data
US 2011/0060255 A1 Mar. 10, 2011

Related U.S. Application Data

(60) Provisional application No. 61/032,949, filed on Feb. 29, 2008.

(51) Int. Cl.
*A61B 8/00* (2006.01)
*G02B 6/30* (2006.01)
*A61H 1/00* (2006.01)
*B06B 1/02* (2006.01)

(52) U.S. Cl.
CPC .................................... *B06B 1/0292* (2013.01)

(58) Field of Classification Search
USPC ................. 600/459, 439, 437, 407, 467, 436; 601/2–4; 310/309, 334; 367/181, 140
See application file for complete search history.

(56) References Cited

U.S. PATENT DOCUMENTS

| | | | | |
|---|---|---|---|---|
| 5,558,092 | A * | 9/1996 | Unger et al. | 600/439 |
| 6,314,057 | B1 | 11/2001 | Solomon et al. | |
| 6,558,330 | B1 | 5/2003 | Ayter et al. | |
| 7,408,283 | B2 * | 8/2008 | Smith et al. | 310/309 |
| 2002/0075098 | A1 | 6/2002 | Khuri-Yakub et al. | |
| 2003/0028109 | A1 | 2/2003 | Miller | |
| 2005/0121734 | A1 | 6/2005 | Degertekin et al. | |
| 2005/0200241 | A1 * | 9/2005 | Degertekin | 310/334 |
| 2006/0122508 | A1 | 6/2006 | Slayton et al. | |
| 2006/0163680 | A1 * | 7/2006 | Chen | 257/416 |
| 2007/0013269 | A1 * | 1/2007 | Huang | 310/334 |
| 2007/0066897 | A1 * | 3/2007 | Sekins et al. | 600/437 |
| 2007/0242567 | A1 | 10/2007 | Daft et al. | |

(Continued)

OTHER PUBLICATIONS

"European Application Serial No. 9716644.1, Extended European Search Report mailed Sep. 26, 2013", 7 pgs.

(Continued)

*Primary Examiner* — Long V Le
*Assistant Examiner* — Lawrence Laryea
(74) *Attorney, Agent, or Firm* — Schwegman Lundberg & Woessner, P.A.

(57) ABSTRACT

A therapeutic ultrasound device may include a substrate, at least one high power capacitive micromachined ultrasonic transducer, and at least one imager transducer comprising a capacitive micromachined ultrasonic transducer. The at least one high power capacitive micromachined ultrasonic transducer and the imager transducer may be monolithically integrated on the substrate.

20 Claims, 4 Drawing Sheets

(56) References Cited

U.S. PATENT DOCUMENTS

| | | | | |
|---|---|---|---|---|
| 2007/0264732 | A1 | 11/2007 | Chen | |
| 2008/0259725 | A1* | 10/2008 | Bayram et al. | 367/181 |
| 2010/0246332 | A1* | 9/2010 | Huang | 367/181 |

OTHER PUBLICATIONS

International Application Serial No. PCT/US09/35601, International Search Report mail Apr. 27, 2009, 1 pgs.

* cited by examiner

THERAPEUTIC ULTRASOUND TRANSDUCER CHIP WITH INTEGRATED ULTRASOUND IMAGER AND METHODS OF MAKING AND USING THE SAME

CROSS-REFERENCE TO RELATED APPLICATIONS

This application is filed under 35 U.S.C. §371 as a U.S. national phase application of PCT/US2009/035601, having an international filing date of Feb. 27, 2009, which claims the benefit of U.S. provisional patent application No. 61/032,949, filed on Feb. 29, 2008, the contents of which are incorporated herein by reference.

TECHNICAL FIELD

The present invention is directed generally to ultrasound devices and methods. More particularly, the present invention is directed to a therapeutic ultrasound transducer chip with an integrated ultrasound imager, and methods of use, for example, in real-time monitoring of a biological object being treated.

BACKGROUND

For therapeutic ultrasound, real-time monitoring of a biological object being treated is of critical importance to the patient's safety and the success of the procedure or operation. While magnetic resonance imaging (MRI) and non-invasive ultrasound imaging have been conventionally used for this purpose, they provide a limited viewing angle and/or images with limited spatial resolution. For many high-precision invasive operations, such as, for example, peripheral thrombolysis, in-situ imaging capability is highly desired.

Some conventional capacitive micromachined ultrasonic transducers insert a dielectric layer between the electrode on the membrane and its counter electrode to prevent the membrane electrode from contacting the counter electrode in a collapse event such as, for example, during an ultrasound transduction. However, the dielectric layer insert between the membrane and the counter electrode increases the effective gap height of the capacitive micromachined ultrasonic transducer, as well as the voltage required to drive the transducer. It may be desirable to minimize the gap height and the required driving voltage of a capacitive micromachined ultrasonic transducer so that the transducer can be employed in minimally-invasive or non-invasive applications, treatments, and/or operations, such as, for example, intravascular procedures including, but not limited to, peripheral thrombolysis This disclosure solves one or more of the aforesaid problems with a therapeutic ultrasound transducer chip having built-in imaging capability and/or a reduced gap height and/or driving voltage.

SUMMARY OF THE INVENTION

In accordance with various aspects, the present disclosure is directed to a therapeutic ultrasound device, which may comprise a substrate, at least one high power capacitive micromachined ultrasonic transducer, and at least one imager transducer comprising a capacitive micromachined ultrasonic transducer. The at least one high power capacitive micromachined ultrasonic transducer and the imager transducer may be monolithically integrated on the substrate.

According to some aspects of the disclosure, a therapeutic ultrasound device may comprise a substrate, at least one high power capacitive micromachined ultrasonic transducer ring integrated on the substrate, and an imager transducer ring comprising an annular array of a plurality of capacitive micromachined ultrasonic transducer elements. The imager transducer ring may be integrated on the substrate, and the imager transducer ring may be outside of the at least one high power capacitive micromachined ultrasonic transducer ring.

DETAILED DESCRIPTION

Figure 1A:
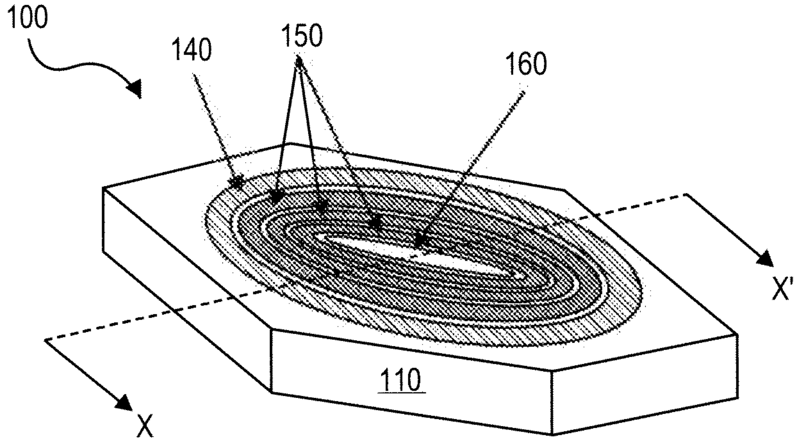
FIG. 1A is a schematic illustration of an exemplary therapeutic ultrasound chip with a built-in ultrasound imager in accordance with various aspects of the disclosure.
Figure 1B:
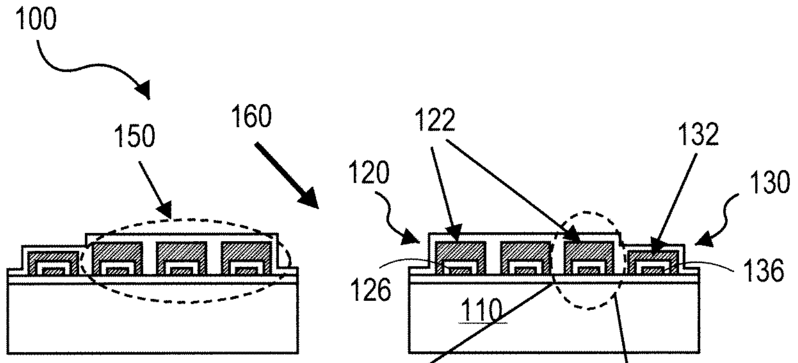
FIG. 1B is a cross-sectional view along line X-X of FIG. 1A.
Figure 1C:
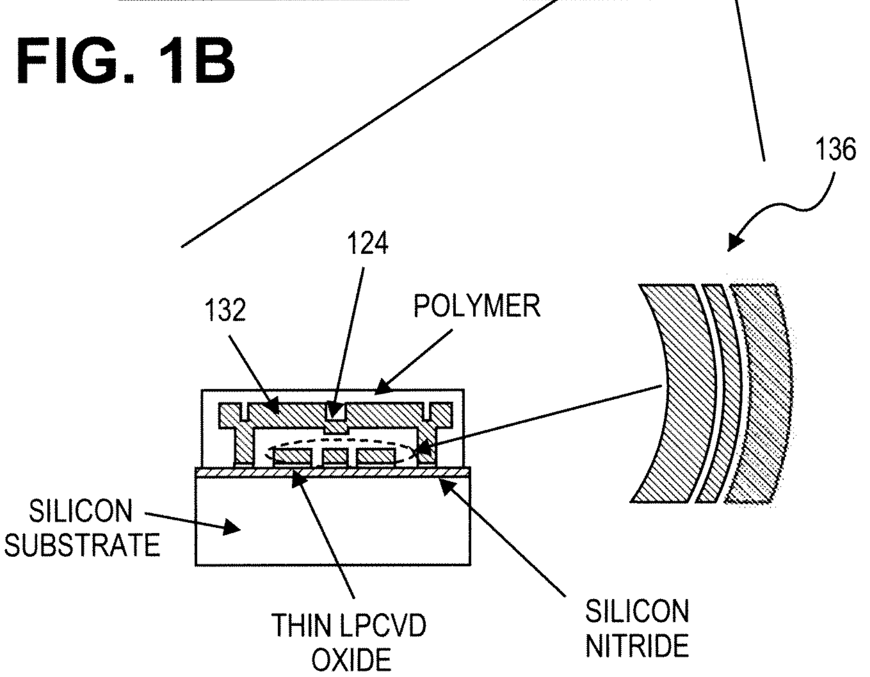
FIG. 1C is an enlarged view of the circled portion of FIG. 1B.

An exemplary embodiment of a therapeutic ultrasound transducer chip 100 with a built-in ultrasound imager is shown in FIG. 1. According to various aspects of the disclosure, the chip 100 may comprise a micromachined substrate 110, for example, a micromachined silicon substrate. The substrate 110 may have a plurality of capacitive micromachined ultrasonic transducers (CMUT) thereon, for example, one or more high power CMUTs 120 and an imager CMUT 130. The one or more high power CMUTs 120 and the imager CMUT 130 are monolithically integrated on the micromachined substrate 110.

The high-power CMUT 120 of the dual-function CMUT chip 100 may include a membrane electrode 122 and a counter electrode 126. According to various aspects of the disclosure, a membrane electrode 122 may comprise a polysilicon film that functions as both the membrane and the electrode. According to some aspects, the membrane electrode 122 may include a membrane comprising silicon nitride, silicon dioxide, poly-germanium, silicon carbide, polysilicon, or the like, and an electrode comprising a metal such as, for example, aluminum, gold, silver, copper, or the like.

Similarly, the imager CMUT 130 may include a membrane electrode 132 and a counter electrode 136. According to various aspects of the disclosure, a membrane electrode 132 may comprise a polysilicon film that functions as both the membrane and the electrode. According to some aspects, the membrane electrode 132 may include a membrane comprising silicon nitride, silicon dioxide, poly-germanium, silicon carbide, polysilicon, or the like, and an electrode comprising a metal such as, for example, aluminum, gold, silver, copper, or the like.

As shown in the inset of FIG. 1, the counter electrode 126 of the high power CMUT 120 may comprise, for example, a pair of spaced polysilicon counter electrodes 128 with an electrically floating polysilicon mat 129 therebetween. According to some aspects, the counter electrode 136 of the imager CMUT 130 may be structured similarly.

Due to the difference in functions between the high power CMUT 120 and the imager CMUT 130, their structures may differ in the membrane thickness and/or the gap height. For example, a thicker membrane 122 and a larger gap height may be used on the high-power CMUT device 120 such that it is capable of delivering a large restoring force/pressure during ultrasound transmission. On the other hand, the membrane 132 of the imager CMUT 130 may be made thinner and more flexible so that it may be sensitive to echo ultrasounds.

According to some aspects, the membrane electrode 122 of the high power CMUT 120 may have a thickness of about 1.6 μm, and a gap height between the membrane electrode 122 and the counter electrode 126 may be about 0.32 μm. According to some aspects, the membrane electrode 132 of the imager CMUT 130 may have a thickness of about 1.0 μm, and a gap height between the membrane electrode 132 and the counter electrode 136 may be about 0.17 μm.

The therapeutic CMUT chip 100 may include a buffering member 124, such as, for example, a polysilicon island, extending from the membrane electrode 122 of the high power CMUT 120 and toward the counter electrode 126 of the high power CMUT 120. The buffering member 124 may be configured to prevent the membrane electrode 122 from contacting the counter electrode 126 in the case of a collapse event. For example, the buffering member may prevent membrane electrode—counter electrode shorting during an ultrasound transduction. The use of the buffering polysilicon island 124 instead of the conventionally used extra dielectric layer inserted between the membrane and the counter electrode may reduce the effective gap height of the high power CMUT, as well as the driving voltage, both of which may be desirable, for example, in interventional procedures. According to some aspects, the gap height may be reduced by about 0.1 micron.

Similarly, the therapeutic CMUT chip 100 may include a buffering member (not shown), such as, for example, a polysilicon island, extending from the polysilicon membrane 132 of the imager CMUT 130 and toward a counter electrode 136 of the imager CMUT 130. The buffering member may be configured to prevent the polysilicon membrane 132 from contacting the counter electrode 136 in the case of a collapse event. For example, the buffering member may prevent membrane electrode—counter electrode shorting during an ultrasound transduction. The use of the buffering polysilicon island instead of the conventionally used extra dielectric layer inserted between the membrane and the counter electrode may reduce the effective gap height of the imager CMUT, as well as the driving voltage, both of which may be desirable, for example, in interventional procedures.

Referring again to FIG. 1, multiple concentric CMUT rings may be integrated on a single therapeutic ultrasound chip of unitary construction. The outermost ring 140 may comprise an imager array made up, for example, of forty-eight or sixty-four imager CMUT elements 130, in which each element can be independently addressed. The remaining inner rings 150 may comprise high power CMUT devices 120 designed to operate at substantially the same resonant frequency. Different from the imager ring 140, which may be divided into multiple small chambers, the high-power CMUT rings 150 may each have a "swim ring" structure comprising one single camber. The one-piece annular membranes 122 of the "swim ring" CMUTs provide a larger effective membrane deformation than a multiple chamber CMUT could provide under the same bias condition. The one-piece annular membrane of the "swim ring" CMUTs may also provide a higher average acoustic energy. In addition to providing simultaneous firing, the multiple high-power CMUT rings 150 may operate as a phase array to deliver electronically-focused ultrasound.

Figure 2:
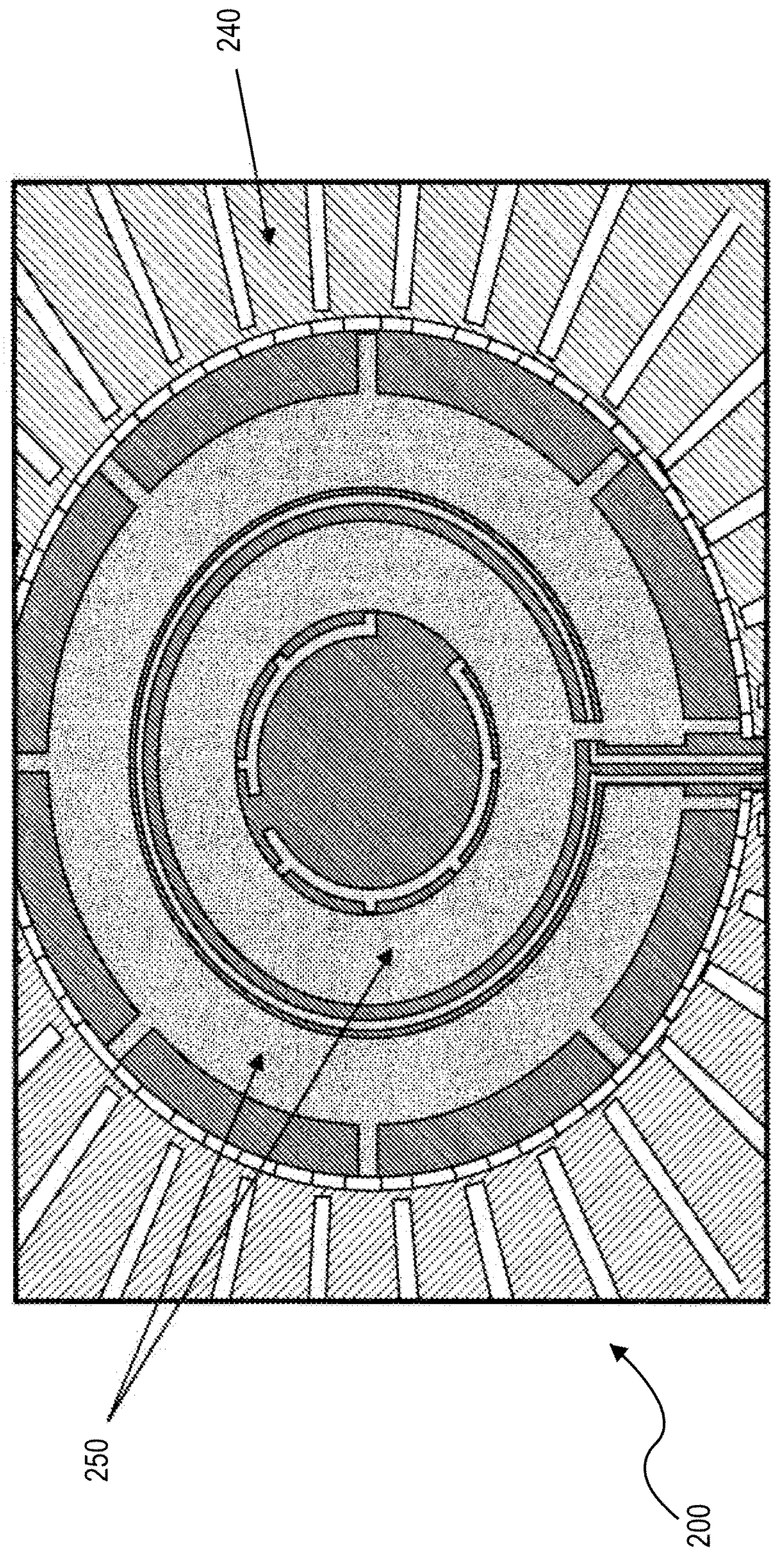
FIG. 2 is a photograph, taken with a scanning electron microscope, of an exemplary therapeutic ultrasound chip with a built-in ultrasound imager in accordance with various aspects of the disclosure.

FIG. 2 shows a scanning electron microscope (SEM) photograph of an exemplary CMUT chip 200 with dual (imaging & therapy) function. As shown, the dual-function CMUT chip 200 comprises two concentric high-power (inner) rings 250 and one annular (outermost) ring 240 comprising an imager array with, for example, 48 imager CMUT elements.

The aforementioned exemplary dual-function therapeutic chips 100, 200 may comprise ultrasound transducer chips with built-in imaging capability. On the therapeutic chips 100, 200, a high-power capacitive micromachined ultrasonic transducer (CMUT) 120 and an imager CMUT 130 are monolithically integrated on a single micromachined silicon substrate 110 for minimally-invasive or non-invasive applications, treatments, and/or operations. For example, the therapeutic chips 100, 200 may be utilized for intravascular procedures including, but not limited to, peripheral thrombolysis. Referring back to FIG. 1, the substrate 110 may include a hole 160 for accommodating a guiding wire used to position the chip 100, 200 during interventional procedures.

Figure 3A:
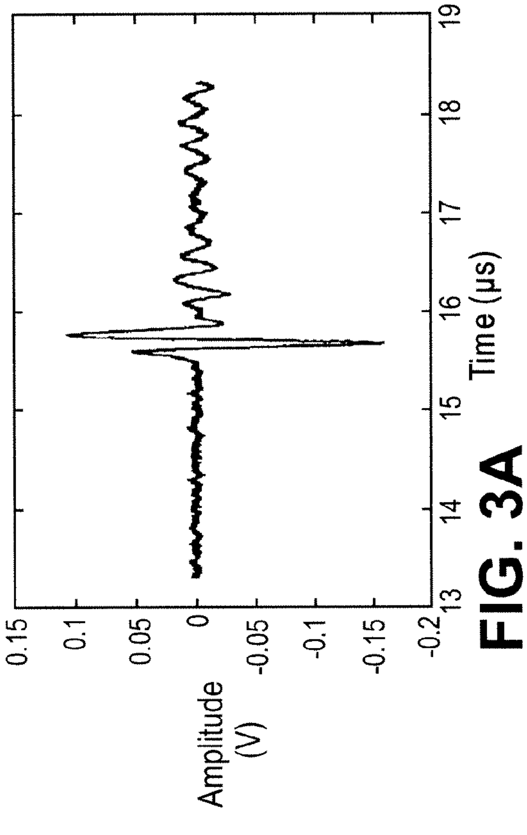
FIGS. 3A and 3B are graphs of time domain and frequency domain signals of an ultrasound transmitted by an imager transducer of the device of FIG. 1 in accordance with various aspects of the disclosure.
Figure 3B:
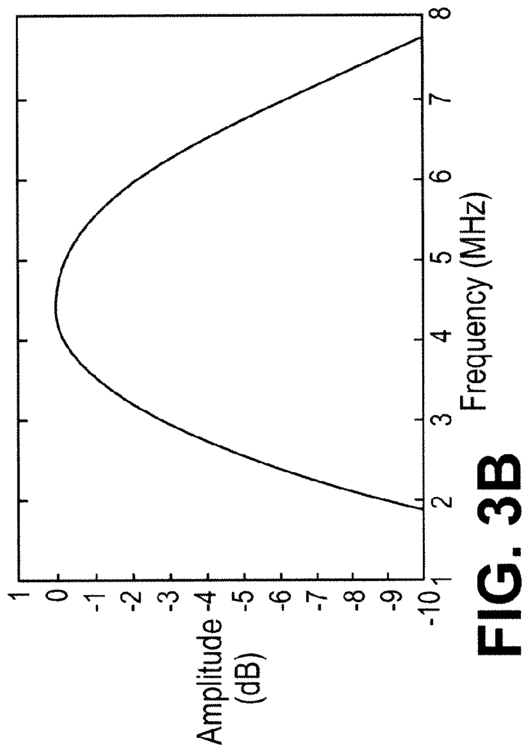
Figure 3C:
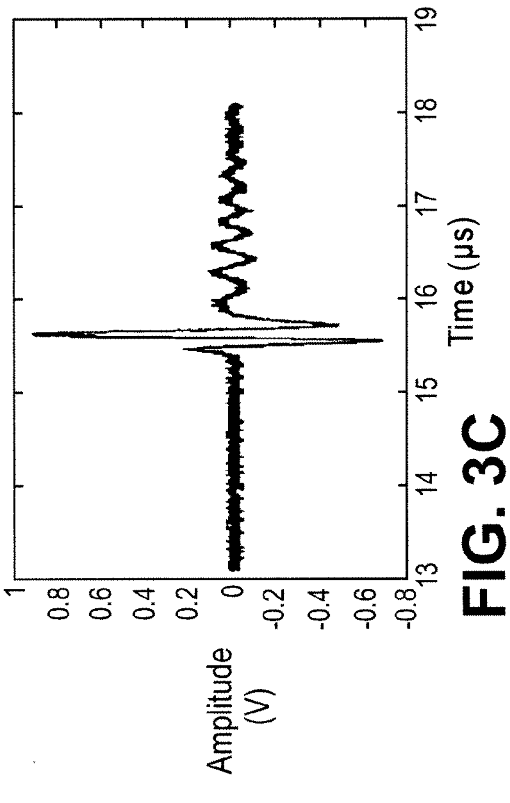
FIGS. 3C and 3D are graphs of time domain and frequency domain signals of an ultrasound transmitted from a commercially-available piezoelectric transducer and received by an imager transducer of the device of FIG. 1 in accordance with various aspects of the disclosure.
Figure 3D:
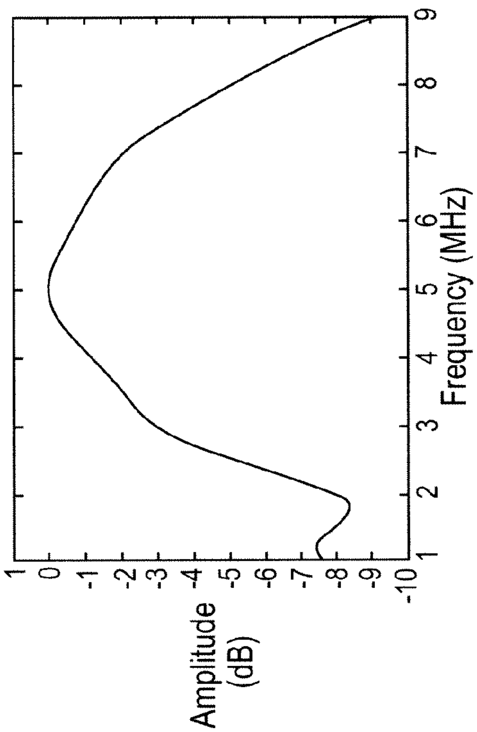

Referring now to FIGS. 3A and 3B, the time domain and frequency domain signals of an ultrasound transmitted by the imager CMUT of the exemplary dual-function therapeutic chip are shown in graphs. The ultrasound signal was recorded by a commercial hydrophone. FIGS. 3C and 3D graphically illustrate the time domain and frequency domain signals of an ultrasound transmitted from a commercial piezoelectric transducer and received by the imager CMUT of the exemplary dual-function therapeutic chip. As illustrated, the capacitive micromachined ultrasonic transducers disclosed herein can generate ultrasound similar to a commercial piezoelectric transducer, but with a broader acoustic bandwidth than that of the commercial transducer.

Figure 4B:
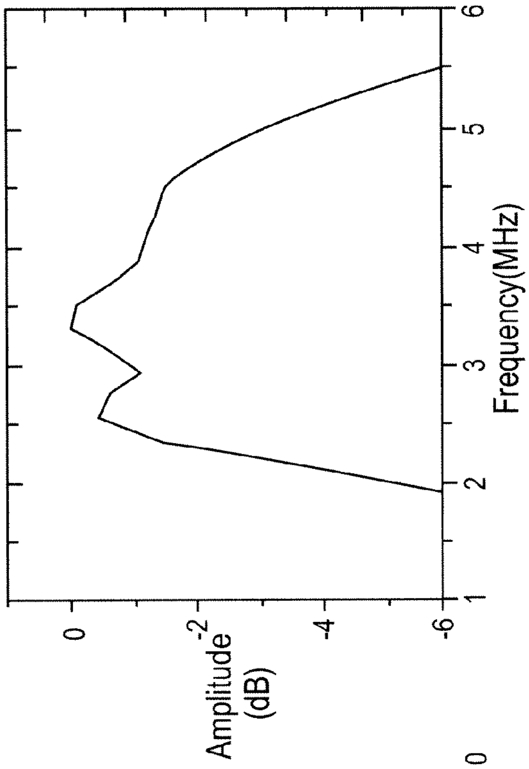
FIGS. 4A and 4B are graphs time domain and frequency domain ultrasound signals transmitted by a high-power transducer of the device of FIG. 1 in accordance with various aspects of the disclosure.
Figure 4A:
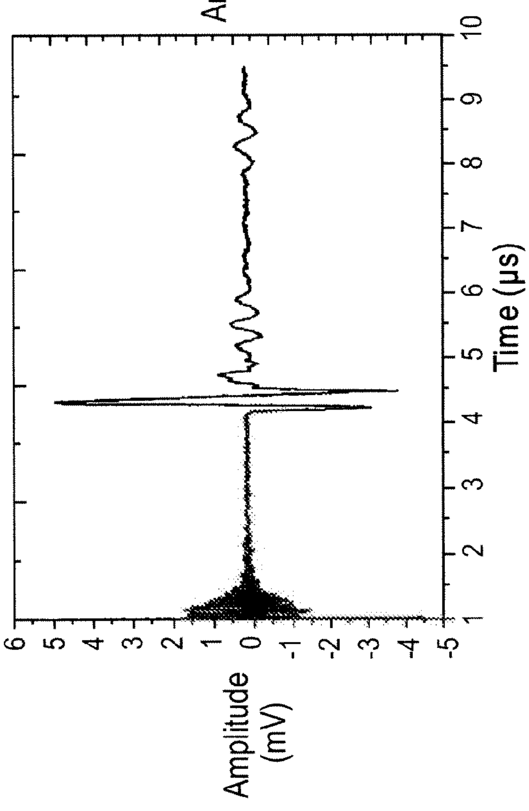

FIGS. 4A and 4B graphically illustrate the time domain and frequency domain ultrasound signals transmitted by one of the high-power CMUT rings of the exemplary dual-function therapeutic chip under excitation of a 50V peak-to-peak, 100 ns-wide impulse with a 20V dc bias. As illustrated, the capacitive micromachined ultrasonic transducers disclosed herein can generate high pressure ultrasound similar to that generated by a commercial piezoelectric ultrasound transducer.

Figure 5:
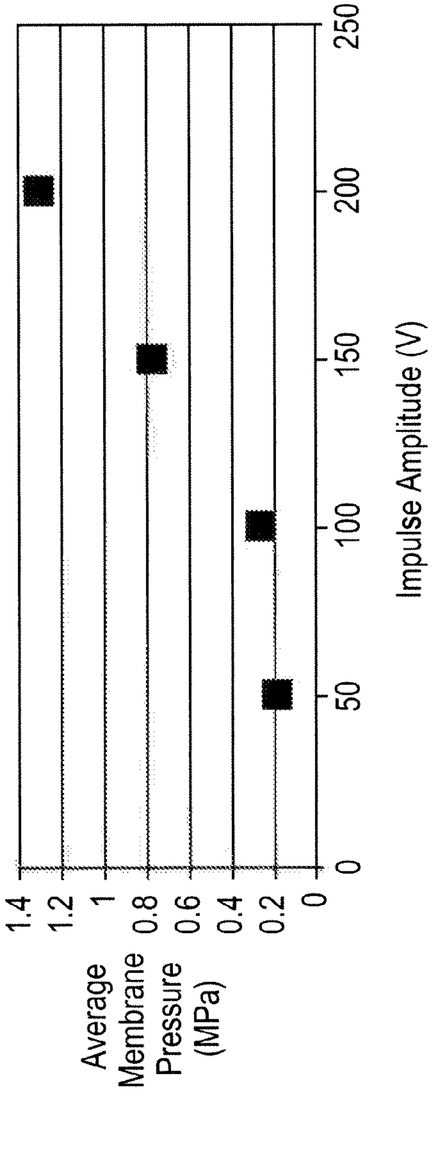
FIG. 5 is a graph of ultrasound pressure transmitted by a high-power transducer of the device of FIG. 1 in accordance with various aspects of the disclosure.

Referring now to FIG. 5, the average peak-to-peak ultrasound pressure (normalized at the CMUT membrane surface) transmitted by a high-power CMUT device of the exemplary dual-function therapeutic chip by an impulse (1 μs-wide) of different amplitude with a 50V dc bias is graphically illustrated.

It will be apparent to those skilled in the art that various modifications and variations can be made to the therapeutic ultrasound transducer chip with an integrated ultrasound imager and methods of the present invention without departing from the scope of the invention. Other embodiments of the invention will be apparent to those skilled in the art from consideration of the specification and practice of the invention disclosed herein. It is intended that the specification and examples be considered as exemplary only.

What is claimed is:

1. A therapeutic ultrasound device comprising:

a substrate;

at least one high power capacitive micromachined ultrasonic transducer having a structure including a membrane electrode and a counter electrode, the membrane electrode having a membrane thickness, the membrane electrode separated from the counter electrode by a gap height within the at least one high power capacitive micromachined ultrasonic transducer; and at least one imager transducer comprising a capacitive micromachined ultrasonic transducer having a structure including a membrane electrode and a counter electrode, the membrane electrode having a membrane thickness, the membrane electrode separated from the counter electrode by a gap height within the at least one imager transducer, the at least one high power capacitive micromachined ultrasonic transducer and the at least one imager transducer being monolithically integrated on the substrate such that the at least one high power capacitive micromachined ultrasonic transducer is disposed laterally with respect to the at least one imager transducer along a surface on the substrate, the at least one high power capacitive micromachined ultrasonic transducer separated from the at least one imager transducer, the structure of the at least one imager transducer differing from the structure of the at least one high power capacitive micromachined ultrasonic transducer in gap height or both membrane thickness and gap height.

2. The device of claim 1, wherein the membrane electrode of the at least one high power capacitive micromachined ultrasonic transducer comprises doped polysilicon.

3. The device of claim 1, wherein the membrane electrode of the at least one high power capacitive micromachined ultrasonic transducer comprises one of silicon nitride, silicon dioxide, poly-germanium, silicon carbide, and polysilicon, and the counter electrode of the at least one high power capacitive micromachined ultrasonic transducer comprise one of aluminum, gold, silver, or copper that are suitable materials for the membrane electrode.

4. The device of claim 1, wherein the at least one high power capacitive micromachined ultrasonic transducer comprises a buffering member extending from the membrane electrode of the at least one high power capacitive micromachined ultrasonic transducer and toward the counter electrode of the at least one high power capacitive micromachined ultrasonic transducer.

5. The device of claim 4, wherein the membrane electrode of the at least one high power capacitive micromachined ultrasonic transducer comprises doped polysilicon.

6. The device of claim 4, wherein the membrane electrode of the at least one high power capacitive micromachined ultrasonic transducer comprises one of silicon nitride, silicon dioxide, poly-germanium, silicon carbide, and polysilicon, and the counter electrode of the at least one high power capacitive micromachined ultrasonic transducer comprise one of aluminum, gold, silver, or copper that are suitable materials for the membrane electrode.

7. The device of claim 4, wherein the buffering member is configured to prevent the membrane electrode of the at least one high power capacitive micromachined ultrasonic transducer from contacting the counter electrode of the at least one high power capacitive micromachined ultrasonic transducer during a collapse event.

8. The device of claim 4, wherein the buffering member is configured to prevent membrane electrode—counter electrode shorting during ultrasound transduction.

9. The device of claim 4, wherein the buffering member includes a buffering polysilicon island.

10. The device of claim 1, wherein a thickness of the membrane electrode of the at least one high power capacitive micromachined ultrasonic transducer is greater than a thickness of a membrane electrode of the at least one imager transducer.

11. The device of claim 10, wherein the thickness of the membrane electrode of the at least one high power capacitive micromachined ultrasonic transducer is about fifty percent greater than the thickness of the polysilicon membrane of the at least one imager transducer.

12. The device of claim 1, wherein a gap height of the at least one high power capacitive micromachined ultrasonic transducer is greater than a gap height of the at least one imager transducer.

13. The device of claim 12, wherein the gap height of the at least one high power capacitive micromachined ultrasonic transducer is about fifty percent greater than the gap height of the at least one imager transducer.

14. A therapeutic ultrasound device comprising:

a substrate, the substrate being a single micromachined substrate;

at least one high power capacitive micromachined ultrasonic transducer ring integrated on the substrate, the at least one high power capacitive micromachined ultrasonic transducer ring having a one-piece membrane common to each high power capacitive micromachined ultrasonic transducer of a plurality of high power capacitive micromachined ultrasonic transducers of the at least one high power capacitive micromachined ultrasonic transducer ring, defining a single chamber; and an imager transducer ring comprising an annular array of a plurality of capacitive micromachined ultrasonic transducer elements, the imager transducer ring being integrated on the substrate, the imager transducer ring being outside of the at least one high power capacitive micromachined ultrasonic transducer ring along a surface on the substrate, the at least one high power capacitive micromachined ultrasonic transducer ring separated from the imager transducer ring.

15. The device of claim 14, wherein the at least one high power capacitive micromachined ultrasonic transducer ring comprises a plurality of substantially concentric rings.

16. The device of claim 15, wherein the plurality of substantially concentric rings operate as a phase array for delivery electronically-focused ultrasound.

17. The device of claim 14, wherein each high power capacitive micromachined ultrasonic transducer ring comprises a one-piece membrane defining a single chamber.

18. The device of claim 14, wherein the annular array comprises 48 capacitive micromachined ultrasonic transducer elements dividing the imager transducer ring into multiple chambers.

19. The device of claim 14, wherein the annular array comprises 64 capacitive micromachined ultrasonic transducer elements dividing the imager transducer ring into multiple chambers.

20. The device of claim 14, wherein high power capacitive micromachined ultrasonic transducers of the high power capacitive micromachined ultrasonic transducer ring differ in structure from imager transducers of the imager transducer ring based on gap height or both membrane thickness and gap height, gap height being distance separating the membrane from a corresponding counter electrode within the respective capacitive micromachined ultrasonic transducer.

* * * * *